United States Patent [19]
Dennilauler et al.

[11] 3,954,853
[45] May 4, 1976

[54] SUBSTITUTED PHENOXY-3-CHLORO-MALEALDEHYDIC ACIDS

[75] Inventors: Rene Jean Dennilauler; Maurice Edgar Pfaff; Pierre Amédée Roman, all of Vincennes, France

[73] Assignee: Eastman Kodak Company, Rochester, N.Y.

[22] Filed: July 9, 1970

[21] Appl. No.: 61,017

Related U.S. Application Data

[62] Division of Ser. No. 649,435, July 26, 1967, Pat. No. 3,579,374.

[52] U.S. Cl. ............................ 260/521 H; 260/519
[51] Int. Cl.² .................................... C07C 65/18
[58] Field of Search ........ 260/521 A, 521 R, 518 R, 260/519, 521 H

[56] References Cited
OTHER PUBLICATIONS

Martin, Chem. Abst., 61, 2414c (1964).
Mowry, J. Am. Chem. Soc., 75, 1909 (1953).
Wasserman et al., ibid, 75, 2527 (1953).

*Primary Examiner*—John F. Terapane
*Attorney, Agent, or Firm*—C. O. Thomas

[57] ABSTRACT

Tanning (hardening) agents in a colloid layer of gelatin or the like are inactive at ordinary temperatures but are activated at temperatures above 70°C. to rapidly tan the colloid in which they are incorporated. Suggested uses are in thermography and photography. Specific examples describe various gelatin layers containing the heat-activated hardeners. The class of useful tanning agents is described by the formula

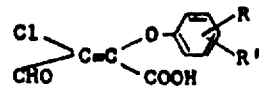

wherein the substituents R and R' are selected from hydrogen and halogen atoms and alkyl, carboxyl, alkoxy, formyl, tertiary amino and sulfo radicals. Some specific new compounds of this class are described.

4 Claims, No Drawings

SUBSTITUTED PHENOXY-3-CHLORO-MALEALDEHYDIC ACIDS

This application is a division of Applicants' copending Application Ser. No. 649,435 filed July 26, 1967, now U.S. Pat. No. 3,579,374 issued May 18, 1971.

BACKGROUND OF THE INVENTION

The invention relates to new chemical compounds and to use of a class of compounds comprising such new compounds as tanning agents for hydrophilic colloids such as gelatin and the like and particularly as tanning agents for hardening hydrophilic colloid layers. As used in various embodiments, the invention relates to thermography and photography, particularly to hardening of gelatin and the like layers in thermographic and photographic recording elements by means of the new class of tanning agents.

Tanning agents of the class used in the present invention are distinguishable over usual tanning agents known in the art, such as formaldehyde, acrolein, glyoxal, dihydroxy ketone, fructose, mucochloric acid, and the like, in that the instant compounds do not tan gelatin compositions having a pH lower than or equal to 5 at ordinary room temperatures as the customary tanning agents do, but they become very rapid tanning agents at activation temperatures above 70°C. By virtue of this selective hot-tanning property, these tanning agents will find uses in which the ordinary room temperature colloid hardeners would not be used. The new tanning agents also may be used to replace conventional hardeners in some uses. The compound 2-phenoxy-3-chloromalealdehydic acid in which, according to the general formula described below, R and R' are both hydrogen atoms, was described by Sawyer in *Proc. Am. Acad. Arts and Sciences*, 1893,29. 242. We have not found reference to other compounds of the class described.

SUMMARY OF THE INVENTION

An object of the invention is to provide new chemical compounds that are useful as gelatin tanning agents and to provide a class of compounds having unique properties as tanning agents for gelatin and related hydrophilic colloids. Another object is to provide improved processes for selective hardening of gelatin at elevated temperatures by means of the subject class of tanning agents. A particular object is to provide improvements in photography and thermography by means of this class of tanning agents and by means of the new tanning processes.

According to the present invention, we have discovered that compounds having the formula:

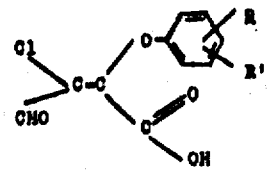

wherein each of R and R' represents a member selected from the group consisting of hydrogen and halogen atoms, alkyl, carboxyl, alkoxy, formyl, tertiary amino and sulfo radicals attached to the ring, are useful as tanning agents for gelatin compositions and the like having the particularly useful property of being practically inert as tanning agents at ordinary room temperatures, e.g. below 50°C, but useful tanning at higher temperatures, i.e. at motivation temperatures above 70°C. when these compositions have a pH lower or equal to 5. Compounds of the class described, when incorporated in colloid layers having a pH lower or equal to 5, for example in layers containing gelatin, will be practically inert as tanning agents indefinitely at temperatures below 50°C. but can be activated as rapid tanning agents simply by elevating the temperature of the layer in which the compound is incorporated to an activating temperature above 70°C., usually in the range from 120°–150°C.

In use as a tanning agent, a compound of the class described is incorporated into a composition with a hydrophilic colloid such as gelatin or the like. For example, an aqueous coating composition containing gelatin and the tanning agent is coated and dried on a supporting surface. At ordinary room temperatures, the tanning agent in the mixed composition will remain inactive indefinitely. To tan the composition then, the temperature is elevated to an activation temperature above 70°C. at which the tanning agent acts rapidly to harden the gelatin.

Concentration of the tanning agent in the composition is relatively minor in proportion, usually in the range from about 1 to 6% by weight, based on dry weight of gelatin or other colloid to be tanned. At activation temperature the tanning agent acts fast, usually achieving the desired degree of hardening in a period from about a few seconds to about 10-15 minutes, depending on various factors such as the degree of hardening desired, selection of the tanning agent, selection of the colloid, relative concentrations in the composition, activation temperature, etc.

The invention can be further understood by reference to the following description of specific examples in which we have set forth in detail our most preferred mode of carrying out the invention, as now contemplated.

DESCRIPTION OF SPECIFIC EMBODIMENTS

A. Preparation of Compounds

EXAMPLE I

Preparation of 2-(p-carboxyphenoxy)-3-chloromalealdehydic acid

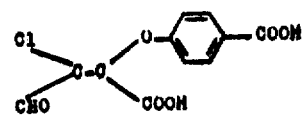

A solution of 120 g. (3 moles) of sodium hydroxide in 1 liter water is cooled to 10°C., then over a period of 15 minutes 138 g. (1 mole) of p-hydroxybenzoic acid is added. After dissolution, the mixture is cooled again to 10°C., then 170 g. (1 mole) of mucochloric acid is added slowly keeping the temperature of the reaction mixture at 10°C., with constant stirring. Then the mixture is allowed to return to room temperature as the stirring is continued for approximately one hour. The solution is poured into a mixture consisting of 1 liter concentrated hydrochloric acid, 1.5 liter cold water, and 500 g. ice. It is allowed to stand for one hour, producing a white precipitate which is separated by filtration and washed twice with 1 liter of cold water at 5°C. The product is then vacuum dried at 50°C., then sifted. A typical yield is 230 g., (86% yield) of white powder having a melting point of 180°C.

Chlorine content calculated: 13%. found: 13.1%.

EXAMPLE II

Following the procedures described in Example I, mucochloric acid is reacted with various substituted phenols of the following formula

wherein the substituents R and R' are as described in the following table:

TABLE

| Product | R | R' | mp°C. | Yield % | Chlorine % theo. | Chlorine % found |
|---|---|---|---|---|---|---|
| 2-(p-tert-pentylphenoxy)-3-chloromalealdehydic acid | p-tert-pentyl | H | 90–95 | 70 | 11.9 | 11.6 |
| 2-(p-octylphenoxy)-3-chloromalealdehydic acid | p-n-octyl | H | 65–70 | 70 | — | — |
| 2-(p-methoxyphenoxy)-3-chloromalealdehydic acid | p-methoxy | H | 95 | 60 | 14.0 | 14.2 |
| 2-(m-pentadecyl)phenoxy-3-chloromalealdehydic acid | m-pentadecylphenoxy | H | 40–45 | 48 | — | — |

In preparing the p-methoxy derivative, the product may be precipitated and dried by the same procedure described in Example I; for the p-tert-pentyl and p-n-octyl derivatives it is more convenient to purify by means of precipitation in a mixture of equal parts ethanol and water.

B. Illustrating Uses as Tanning Agent

EXAMPLE III

To an aqueous 5% solution of gelatin is added 3 parts by weight per 100 parts gelatin of the hot-tanning agent 2-p-carboxyphenoxy-3-chloromalealdehydic acid. The tanning agent is added as a 6% solution in equal parts ethanol and water. Also added is a 1% by volume of a 15% aqueous saponin solution; pH is adjusted to 7 with one-fourth normal sodium hydroxide solution. The final solution is coated by a conventional coating procedure on a sheet of plain white bleached pulp paper at a rate of 20 mg. dried gelatin per dm². The pH of the coated gelatin is about 5 due to the acidity of the paper. The coating is dried and then tanned with heat by applying a pressing iron to the layer of dried gelatin for 1–2 seconds. The iron is heated to a temperature of 150°C. After heating, the melting point of the treated gelatin coating is determined by dipping the coated and treated sample into an agitating tank filled with water and gradually raising the temperature of the water at a rate of 3°C. per minute. Melting point of the layer which has been coated and subsequently heat treated is over 100°C. A control coating containing no tanning agent, after the same heat treatment melts at about 30°C. Before heat treatment the coating with tanning agent melts at about 30°C. and after three months storage at room temperatures only slight variations in the melting point are detected.

A paper sheet coated and tanned as in Example I is useful to replace supports for matrices used in processes such as those described in French Pat. Nos. 980,481 and 1,092,692 in which the supports described consisted of paper coated on both sides with polyethylene. Supports prepared as in Example III are generally equivalent to the polyethylene coated supports with regard to smoothness and operability. As compared with preparation of polyethylene coated supports, the present supports are easier to manufacture and could be produced by much simpler manufacturing machinery. Matrices prepared according to the patents mentioned above comprise an emulsion layer coated on the support which is to be differentially hardened during processing. A particular advantage for this use of a support prepared as described in Example III is its stability and freedom from contamination of the emulsion layer by migration of hardeners from the support gelatin layer to the emulsion layer.

Supports similar to that prepared in Example III may also be used as a gel-subbed support for various photographic emulsions. For example, a subbing of gelatin containing a hot-tanning agent of the class described would be coated on a photographic film support and then tanned rapidly by heating, for example by contacting with a heated iron as described in Example III, or hardening of the sub might be achieved during drying simply by employing drying temperatures above 100°C. to effect simultaneously both drying and hot-tanning.

A "thermo-tanned" layer, such as that described in Example III coated on a support and tanned by heat, can be used for preparing photographic products for receiving silver images by diffusion transfer, the untanned negative emulsion layer being able to be applied onto the tanned layer and then removed after development and diffusion transfer by means of washing with tepid water.

A support with a tanned gelatin layer such as the one described in Example III can be used in photomechanical reproduction, for example, in photolithographic processes used for offset printing such as those described in French Pat. Nos. 1,092,963 and 1,158,449 in which matrices are used that have a photographic emulsion layer coated on a polyethylene treated support. The polyethylene coated support can be replaced in such processes by a support sheet such as the one described in Example III. In Example III we have illustrated the invention by coating a gelatin layer on paper and then tanning gelatin layer. It will be understood that gelatin layers containing the tanning agent can also be coated on other suitable supports such as film supports of cellulose acetate, polyesters, and the like as well as other supports of glass, metal, wood, and the like.

EXAMPLE IV

This example illustrates use of gelatin layers tanned in accordance with the invention in a thermographic process. A solution is prepared consisting of 500 g. of 15% aqueous solution of bone gelatin, 1 liter water, 17 ml. of 15% saponin solution and the pH is adjusted to 7 with one-fourth normal sodium hydroxide. There is then added 2.25 g. of 2-(p-methoxyphenoxy)-3-chloromalealdehydic acid in solution in a mixture of 100 ml. of water and 100 ml. ethanol. Two grams of Prussian Blue are added to the solution. The finished solution is coated on paper at a coverage of 50 mg./dm$^2$ of dry gelatin. The pH of the coated gelatin is about 5. The layer is then dried and exposed in a thermographic copying machine imagewise to heat the gelatin imagewise. The layer is washed with tepid water at 33°–40°C. which washes away gelatin in the unheated areas and forms a tanned gelatin image of blue color in the exposed areas.

In the foregoing description we have mentioned that activation temperatures for the hot-tanning agents is above 70°C. and the agents are inactive at room temperature. It should be explained that the rate of tanning may vary at various temperatures above 70°C. For example, at a lower activation temperature above 70°C., say at 100°C., the rate of hardening may be much slower than at a higher temperature say at 150° or 175°C. For most of the tanning agents of the class described, the most advantageous temperature for tanning will be in the range from 120°–150°C. and useful activation temperatures may vary from about 100°C. up to about 200°C. Useful concentrations of the tanning agent in the colloid layer for most embodiments will be in the range from about 1 to about 6 parts tanning agent per 100 parts of dry colloid in the coating composition and for most uses the optimum concentration will be around 3 parts per hundred. Our tanning agents may be used as hardeners in photographic silver halide emulsion layers and in gelatin layers coated over silver halide emulsion layers. In such cases, use of these particular hardeners is advantageous because hardening can be delayed until after photographic processing. During processing the solutions will easily penetrate the colloid layers to facilitate rapid processing and the layer can then be hardened after processing to produce a finished photograph with a hardened colloid layer. Thus, the hardener can be incorporated in the emulsion during manufacture and its hardening effect can be delayed until after processing. The tanning agents or hardeners can be used to harden baryta layers used as undercoats in photographic printing papers instead of conventional hardeners. The present hardeners have the distinct advantage that they do not migrate to adjacent layers. Thus, they will not contaminate an adjacent layer such as a silver halide layer which might be coated over a layer containing the tanning agent, such as a baryta layer or a gelatin sub.

The invention has been described above with reference mainly to gelatin as a typical hydrophilic colloid that can be hardened by the tanning agents of the invention. More broadly, however, our invention includes uses of the class of tanning agents described when they are used as hardeners with other colloid compositions, for example with casein, albumin and similar natural hydrophilic colloids; with synthetic polymers useful as hydrophilic colloids, such as copolymers of acrylamide with other vinyl monomers such as methacrylic acid, allylacetoacetate, allylacetoacetamide and the like, imidized polyacrylamide, synthesized ampholytic polypeptides, polyoxyalkylene compounds, sulphobenzoate derivatives of cellulose and cellulose esters, polyvinyl alcohol derivatives and the like. The hardeners are effective in mixtures of hydrophilic colloids, for example in a mixture of gelatin with a synthetic polymer of the kind described above, or a mixture of other colloids.

It will be understood that modifications and variations may be made within the scope of the invention as described above and as defined in the following claims.

We claim:

1. The chemical compound 2-(p-carboxyphenoxy)-3-chloromalealdehydic acid.

2. The chemical compound 2-(p-tert-pentylphenoxy)-3-chloromalealdehydic acid.

3. The chemical compound 2-(p-octylphenoxy)-3-chloromalealdehydic acid.

4. The chemical compound 2-(m-pentadecylphenoxy)-3-chloromalealdehydic acid.

* * * * *